(12) United States Patent
Hibbs et al.

(10) Patent No.: US 7,141,968 B2
(45) Date of Patent: Nov. 28, 2006

(54) INTEGRATED SENSOR SYSTEM FOR MEASURING ELECTRIC AND/OR MAGNETIC FIELD VECTOR COMPONENTS

(75) Inventors: Andrew D. Hibbs, La Jolla, CA (US); Robert Matthews, San Diego, CA (US); David Matthew Jabson, San Diego, CA (US)

(73) Assignee: Quasar Federal Systems, Inc., San Diego, CA (US)

( * ) Notice: Subject to any disclaimer, the term of this patent is extended or adjusted under 35 U.S.C. 154(b) by 49 days.

(21) Appl. No.: 10/959,480

(22) Filed: Oct. 7, 2004

(65) Prior Publication Data

US 2005/0073302 A1 Apr. 7, 2005

Related U.S. Application Data

(60) Provisional application No. 60/509,423, filed on Oct. 7, 2003.

(51) Int. Cl.
*G01R 33/02* (2006.01)
*G01R 27/26* (2006.01)

(52) U.S. Cl. ........................ 324/260; 324/247; 324/686

(58) Field of Classification Search ................ 324/244, 324/258, 260, 202, 658, 686, 690, 691, 457, 324/458, 247; 343/703, 725
See application file for complete search history.

(56) References Cited

U.S. PATENT DOCUMENTS

| | | | |
|---|---|---|---|
| 3,500,823 A | 3/1970 | Richardson et al. | |
| 3,565,060 A | 2/1971 | Sipple | |
| 3,620,208 A | 11/1971 | Higley et al. | |
| 3,715,660 A | 2/1973 | Ruhnke | |
| 3,722,677 A | 3/1973 | Lehnert | |
| 3,744,482 A | 7/1973 | Kaufman et al. | |
| 3,815,000 A | 6/1974 | Phillips et al. | |
| 3,880,146 A | 4/1975 | Everett et al. | |
| 3,882,846 A | 5/1975 | Fletcher et al. | |
| 3,923,042 A | 12/1975 | Hajdu et al. | |
| 3,986,109 A * | 10/1976 | Poduje | 324/662 |
| 4,023,408 A | 5/1977 | Ryan et al. | |
| 4,248,244 A | 2/1981 | Charnitski et al. | |
| 4,277,751 A * | 7/1981 | Lawson et al. | 324/254 |

(Continued)

FOREIGN PATENT DOCUMENTS

CA 2428250 11/2003

(Continued)

OTHER PUBLICATIONS

Clayton et al., "Absolute Calibration of Antennas at Extremely Low Frequencies," IEEE Transactions on Antennas and Propagation, vol. AP-21, No. 4, pp. 514-523, Jul. 1973.

(Continued)

*Primary Examiner*—Michael Cygan
*Assistant Examiner*—Kenneth J. Whittington
(74) *Attorney, Agent, or Firm*—Diederiks & Whitelaw PLC

(57) ABSTRACT

A compact sensor system integrates electric and/or magnetic field sensors to accurately measure, with a high level of sensitivity, one or more electric and magnetic vector components of fields. The electric and magnetic field data can be utilized separately or combined. The sensor system is self-contained so as to include a built-in power source, as well as data storage and/or transmission capability. The integrated sensor system also preferably includes a global positioning system (GPS) to provide timing and position information, a sensor unit which can determine the orientation and tilt of the sensor system, and self-calibrating structure which produces local electric and/or magnetic fields used to calibrate the sensor system following deployment.

18 Claims, 2 Drawing Sheets

U.S. PATENT DOCUMENTS

| | | | |
|---|---|---|---|
| 4,346,384 A | | 8/1982 | Raab |
| 4,419,622 A | * | 12/1983 | Cuneo et al. ............... 324/629 |
| 4,478,223 A | | 10/1984 | Allor |
| 4,569,357 A | | 2/1986 | Sanz et al. |
| 4,580,576 A | | 4/1986 | Blackwood |
| 4,581,821 A | | 4/1986 | Cahalan et al. |
| 4,588,993 A | * | 5/1986 | Babij et al. ................. 342/351 |
| 4,593,702 A | | 6/1986 | Kepski et al. |
| 4,602,639 A | | 7/1986 | Hoogendoorn et al. |
| 4,669,479 A | | 6/1987 | Dunseath, Jr. |
| 4,688,141 A | | 8/1987 | Bernard et al. |
| 4,733,242 A | | 3/1988 | de Rosa |
| 4,785,237 A | | 11/1988 | Cox |
| 4,801,866 A | | 1/1989 | Wixley |
| 4,806,851 A | | 2/1989 | Krider et al. |
| 4,850,370 A | | 7/1989 | Dower |
| 4,873,483 A | | 10/1989 | Ostrander |
| 5,001,594 A | | 3/1991 | Bobbio |
| 5,015,906 A | | 5/1991 | Cho et al. |
| 5,036,334 A | | 7/1991 | Henderson et al. |
| 5,039,312 A | | 8/1991 | Hollis, Jr. et al. |
| 5,090,643 A | | 2/1992 | Spears |
| 5,119,404 A | | 6/1992 | Aihara |
| 5,184,215 A | | 2/1993 | Barker |
| 5,191,891 A | | 3/1993 | Righter |
| 5,229,593 A | | 7/1993 | Cato |
| 5,289,822 A | | 3/1994 | Highe et al. |
| 5,304,941 A | | 4/1994 | Tateishi |
| 5,315,232 A | * | 5/1994 | Stewart ........................ 324/72 |
| 5,325,073 A | | 6/1994 | Hasegawa |
| 5,336,999 A | | 8/1994 | Mansfield et al. |
| 5,458,116 A | | 10/1995 | Egler |
| 5,485,092 A | | 1/1996 | Fortin |
| 5,488,677 A | | 1/1996 | Tokano |
| 5,574,805 A | | 11/1996 | Toba et al. |
| 5,632,280 A | | 5/1997 | Leyde et al. |
| 5,645,527 A | | 7/1997 | Beck |
| 5,646,525 A | | 7/1997 | Gilboa |
| 5,650,750 A | | 7/1997 | Leyde et al. |
| 5,670,870 A | | 9/1997 | Muramatsu |
| 5,699,015 A | | 12/1997 | Dotson et al. |
| 5,734,296 A | | 3/1998 | Dotson et al. |
| 5,751,192 A | | 5/1998 | Main |
| 5,781,003 A | | 7/1998 | Kondo |
| 5,795,293 A | | 8/1998 | Carim et al. |
| 5,798,673 A | | 8/1998 | Griffith et al. |
| 5,896,035 A | | 4/1999 | Takahashi |
| 5,947,920 A | | 9/1999 | Beck |
| 6,052,615 A | | 4/2000 | Feild et al. |
| 6,096,220 A | | 8/2000 | Ohkawa |
| 6,111,466 A | | 8/2000 | Mokhtar et al. |
| 6,134,424 A | | 10/2000 | Nishihori et al. |
| 6,215,294 B1 | | 4/2001 | Coleman |
| 6,242,911 B1 | * | 6/2001 | Maschek .................... 324/247 |
| 6,246,367 B1 | | 6/2001 | Markson et al. |
| 6,262,631 B1 | | 7/2001 | Li |
| 6,411,108 B1 | | 6/2002 | Douglas et al. |
| 6,438,413 B1 | | 8/2002 | Taheri |
| 6,472,888 B1 | | 10/2002 | Oguma et al. |
| 6,551,252 B1 | | 4/2003 | Sackner et al. |
| 6,597,942 B1 | | 7/2003 | Yonce |
| 6,611,168 B1 | | 8/2003 | Denison et al. |
| 6,674,281 B1 | * | 1/2004 | Shieh ....................... 324/244.1 |
| 6,686,800 B1 | | 2/2004 | Krupka |
| 6,721,591 B1 | | 4/2004 | Wei et al. |
| 6,754,523 B1 | | 6/2004 | Toole |
| 6,755,795 B1 | | 6/2004 | Marmaropoulos et al. |
| 6,760,615 B1 | | 7/2004 | Ferek-Petric |
| 6,791,311 B1 | | 9/2004 | Murphy et al. |
| 6,807,438 B1 | | 10/2004 | Brun del Re et al. |
| 6,842,006 B1 | * | 1/2005 | Conti et al. ................. 324/350 |
| 6,861,838 B1 | * | 3/2005 | Kawase ....................... 324/249 |
| 2002/0038092 A1 | | 3/2002 | Stanaland et al. |
| 2003/0036691 A1 | | 2/2003 | Stanaland et al. |
| 2003/0214408 A1 | | 11/2003 | Grajales et al. |
| 2003/0224685 A1 | | 12/2003 | Sharma |
| 2003/0231141 A1 | * | 12/2003 | Alden et al. ................. 343/893 |
| 2004/0070446 A1 | | 4/2004 | Krupka |
| 2004/0073104 A1 | | 4/2004 | Brun del Re et al. |
| 2004/0254435 A1 | | 12/2004 | Mathews et al. |

FOREIGN PATENT DOCUMENTS

| | | |
|---|---|---|
| GB | 2353594 | 2/2001 |
| WO | 03/048789 | 6/2003 |
| WO | 03/079897 | 10/2003 |

OTHER PUBLICATIONS

Degauque et al. (Editors), "Electromagnetic Compatibility," Simulation Techniques and Sensors, Oxford University Press, pp. 614-643, 1993.

Filloux, "Electric Field Recording on the Sea Floor with Short Span Instruments," J. Geomag. Geoelectr., vol. 26, pp. 269-279, 1974.

Harrison, "An Antenna Electrometer System for Atmospheric Electrical Measurements," Rev. Sci. Instrum., American Institute of Physics, vol. 68, No. 3, pp. 1599-1603, Mar. 1997.

Hill, et al., "Electric Field Strength," The Measurement, Instrumentation, and Sensors Handbook, IEEE Press, pp. 47.1-47.13.

Pedersen et al., "Electric Field Measurements in a Tenous Plasma with Spherical Double Probes," Geophysical Monograph 103, Measurement Techniques in Space Plasmas: Fields, American Geophysical Union, pp. 1-12, 1998.

Author Unknown, "Ultra Low Input Bias Current Instrumentation Amplifier," Burr-Brown Corp., pp. 1-9, 1994.

Byrne et al., "Ground-Based Instrumentation for Measurement of Atmospheric Conduction Current and Electric Field at the South Pole," Journal of Geophysical Research, vol. 98, No. D2, pp. 2611-2618, Feb. 20, 1993.

Clippingdale et al., "Ultra-High Impedance Voltage Probes and Non-Contact Electrocardiography," Sensors: Technology, Systems and Applications, 1st Edition, IOP Publ. Ltd., pp. 469-472, 1991.

Clippingdale et al., "Non-Invasive Dielectric Measurements with the Scanning Potential Microscope," J. Phys. D: Appl. Phys., IOP Publ. Ltd., vol. 27, pp. 2426-2430, 1994.

Clippingdale et al., "Ultrahigh Impedance Capacitively Coupled Heart Imaging Array," Rev. Sci. Instrum., American Institute of Physics, vol. 65, No. 1, pp. 269-270, Jan. 1994.

Geddes, L. A., "Electrodes and the Measurement of Bioelectric Events," Wiley-Interscience, pp. 97-106, 1972.

Harland et al., "Electric Potential Probes—New Directions in the Remote Sensing of the Human Body," Meas. Sci. and Technol., Institute of Physics Publishing, IOP Publ. Ltd., vol. 13, pp. 163-169, 2002.

Harland et al., "Remote Detection of Human Electroencephalograms Using Ultrahigh Input Impedance Electric Potential Sensors," Applied Physics Letters, American Institute of Physics, vol. 81, No. 17, pp. 3284-3286, Oct. 2002.

Harland et al., "Resolution Ambulatory Electrocardiographic Monitoring Using Wrist-Mounted Electric Potential Sensors," Meas. Sci. and Technol., Institute of Physics Publishing, IOP Publ. Ltd., vol. 14, pp. 923-928, 2003.

Horowitz et al. "The Art of Electronics," 2nd Edition, Cambridge University Press, pp. 96-98, 183-187, 193-207, 209-210, 1989.

Maynard, "Electric Field Measurements in Moderate to High Density Space Plasmas with Passive Double Probes," Geophysical Monograph, American Geophysical Union, vol. 103, pp. 13-27, 1998.

Nunez, P. L., "Electric Fields of the Brain: The Neurophysics of EEG," Oxford University Press, pp. 197-198, 1981.

Nunez, P.L. et al. "Spatial-Temporal Structures of Human Alpha Rhythms: Theory, Microcurrent Sources, Multiscale Measurements, and Global Binding of Local Networks," Human Brain Mapping, Wiley-Liss, Inc., vol. 13, pp. 125-164, 2001.

Prance et al., "Electrometer Arrays: Sensing of Spatio-Temporal ELF Fields," Proc. Marelec, 3.4, 1997.

Prance et al., "Non-Contact VLSI Imaging Using a Scanning Electric Potential Microscope," Meas. Sci. Technol. vol. 11, pp. 1229-1235, 1998.

Prance et al., "An Ultra-Low-Noise Electrical-Potential Probe for Human-Body Scanning," Meas. Sci. and Technol., IOP Publ. Ltd., vol. 11, pp. 1-7, 2000.

Richardson, P.C., "The Insulated Electrode: A Pasteless Electrocardiographic Technique," 20th Annual Conference on Engineering in Medicine and Biology, pp. 15.7, 1967.

Srebo, R., "Localization of Visually Evoked Cortical Activity in Humans," J. Physiology, vol. 360, pp. 233-246, 1985.

Srinivisan et al., "Spatial Sampling and Filtering of EEG with Spline Laplacians to Estimate Cortical Potentials," Brain Topography, Human Sciences Press, Inc., vol. 8, No. 4, pp. 355-366, 1996.

Von Helmholtz, H., Ann. Phys. Chem., vol. 29, pp. 211-233, 1853.

* cited by examiner

INTEGRATED SENSOR SYSTEM FOR MEASURING ELECTRIC AND/OR MAGNETIC FIELD VECTOR COMPONENTS

CROSS-REFERENCE TO RELATED APPLICATION

The present application claims the benefit of U.S. Provisional Patent Application Ser. No. 60/509,423 entitled "Integrated Electric and Magnetic Field Sensor" filed Oct. 7, 2003.

STATEMENT OF GOVERNMENT INTEREST

The U.S. Government has a paid-up license in this invention and the right in limited circumstances to require the patent owner to license others on reasonable terms as provided for by the terms of DARPA Contract Nos. F33615-02-C-1260 and DAAH01-02-C-R225.

BACKGROUND OF THE INVENTION

1. Field of the Invention

The present invention pertains to measuring at least magnetic fields and, more particularly, to an integrated sensor system for measuring vector components of magnetic fields, preferably along with electric fields.

2. Discussion of the Prior Art

Measurements of electric and magnetic fields at low frequencies, generally less than 1 kHz, have been made for many years using discrete sensors to measure the electric field (E-field) and magnetic field (B-field) separately. In addition, it has been proposed to integrate electric and magnetic components into a single sensor. However, when a high level of sensitivity is required, individual sensors are invariably utilized to measure desired components of each field. For example, to make a magnetotelluric measurement, individual magnetic induction sensors are laid on the ground at a separation of a few meters and rods are buried in the ground nearby to measure the horizontal electric field. In most cases, the respective sensors must all be aligned relative to one another and mounted with sufficient rigidity to minimize relative motion. Depending on the accuracy required, such an installation can take a significant time to complete and requires an area in the order of 10 m² to operate.

Prior high sensitivity induction sensors have been too large to integrate together. While one cylindrical object of length even up to 2 m is relatively easy to handle and transport, a system comprised of two or three such sensors at right angles to each other, if even contemplated, would be very cumbersome. In addition, prior induction sensors designed for detection of small low frequency signals had diameters in the order of 3 cm or more. Simply stated, prior induction sensors and arrangements that involve them are quite large and sub-optimal, while being inefficient to set-up and operate.

In many applications, the ability to reasonably employ a dual field sensor system will depend on the compactness and even weight of the system. These applications include the installation of dual field sensors in aircraft, spacecraft and ground vehicles, as well as situations where the sensor system must be deployed in a certain way such as hand or air-drop deployment situations. The time consuming set-up and lack of compactness in prior proposals has essentially limited the use of collected E-field and B-field information to geophysical applications, such as magnetotellurics and the measurement of lightning, wherein the sensors can be positioned over a relatively wide area.

When electric and magnetic field data has been collected together, the objective has generally been to collect an individual field parameter as a record of a specific physical phenomena, e.g. lightning. However, the present Applicants have recognized that specific vector components of known orientation in the electric and magnetic field data can be combined to produce a reduced output. For instance, new combined electric and magnetic measurement applications arise, including using information in one measurement channel, e.g., an electric field vector component, to reduce environmental noise in other channels, e.g., multiple magnetic field vector components. In addition, the ratio of various signals in different electric and magnetic axes can be determined to provide source characteristic capabilities.

Based on the above, there exists a need to combine one or more electric field sensors with one or more magnetic field sensors to establish an integrated sensor system which is compact in nature in order to employ the sensor system in a wide range of applications. In addition, there exists a benefit to be able to readily combine different data from individual axes of such an integrated sensor system in order to take advantage of particular relationships between the electric and magnetic fields that pertain to certain properties of the environment or source(s) of interest.

SUMMARY OF THE INVENTION

The present invention is directed to an integrated and compact sensor system for determining electric and/or magnetic vector component information of fields. Sensors are maintained at fixed, well defined relative positions for generating signals from which the vector information is determined. Different data from individual axes of the integrated sensor system is preferably combined in a manner which takes advantage of particular relationships between the electric and magnetic fields.

In accordance with a preferred embodiment of the invention, multiple sensors are employed for measuring the electric and/or magnetic fields, with the multiple sensors being preferably, rigidly connected together along defined, intersecting axes, while communicating with a controller for processing and analyzing the data. In accordance with the most preferred embodiment of the invention, the sensor system is self-contained so as to include a built-in power source, as well as data storage and/or transmission capability, such that the system can operate without an electrically conducting contact with the surrounding environment.

In addition to the electric and/or magnetic field sensors, the integrated sensor system also preferably includes a global positioning system (GPS) to provide timing and position information. Furthermore, a sensor unit which can determine the orientation and tilt of the sensor system can be incorporated as well. Also, the sensor system can be self-calibrating, wherein structure is provided to produce local electric and/or magnetic fields which are used to calibrate the sensor system following deployment.

Additional objects, features and advantages of the present invention will become more readily apparent from the following detailed description of preferred embodiments when taken in conjunction with the drawings wherein like reference numerals refer to corresponding parts in the several views.

DETAILED DESCRIPTION OF THE PREFERRED EMBODIMENTS

The present invention provides advances in connection with establishing a compact sensor system that can measure multiple vector components of both electric and magnetic fields at very high sensitivity. By a "compact" sensing system it is meant that the region over which a particular field is measured is small relative to the spatial variations in the field that are of interest, and/or is sufficiently compact that a system that measures multiple components of the field is of a convenient size. As will become fully evident below, the compact nature and arrangement of the various sensors allows the sensors to intersect at a common center, while enabling minimum lateral offsets between the sensors.

Figure 1:
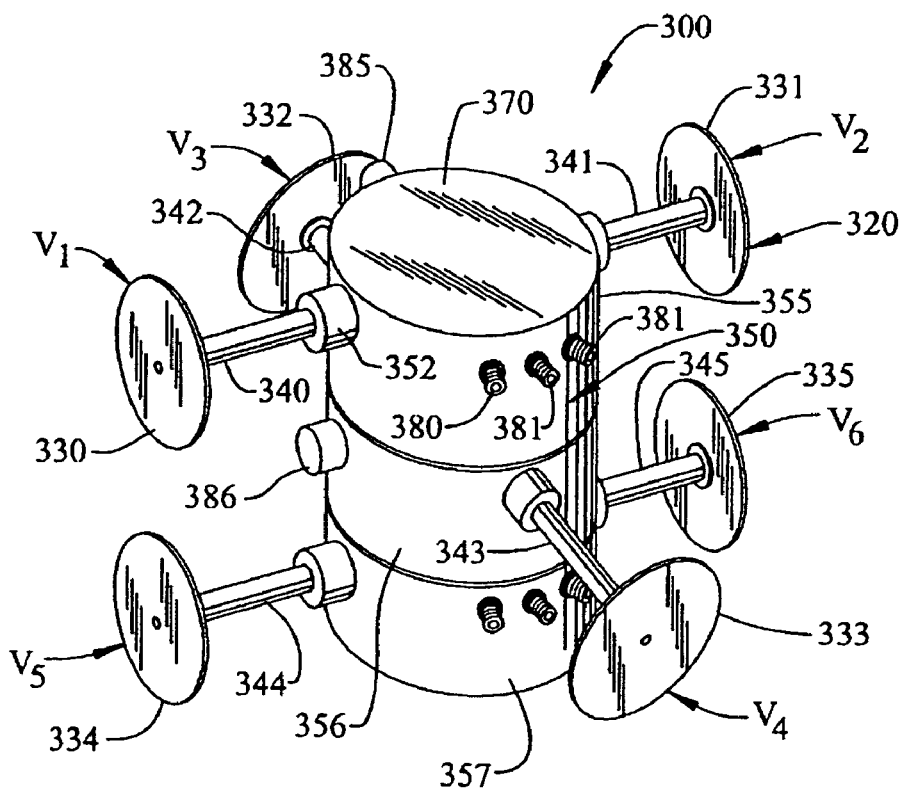
FIG. 1 is a perspective view of an integrated electric (E) and magnetic (B) field sensor constructed in accordance with a preferred embodiment of the invention.

An example of a multi-axis, combined E-field and B-field sensor system 300 built according to a preferred embodiment of the invention is shown in FIG. 1. In this system, three orthogonal axes of an electric field are measured with various capacitive sensors 330–335 arranged as pairs in orthogonal oriented directions. To measure the electric field, it is only necessary to measure the potential at two points, subtract one result from the other, and divide by the physical distance, d, between the two points, and multiply by a calibration constant k which is close to unity to allow for the design of the sensor, with k being readily determinable by testing the sensor in a known field.

$$E = k \frac{V_1 - V_2}{d} \quad [1]$$

As will be detailed more fully below, the two measurements can be made by completely different sensors or by connecting two separate potential sensors to an appropriate amplifier with a differential input. The voltage of one sensor can be subtracted in a pair-wise fashion from multiple other sensors to provide the electric field in the direction of the vector joining the measurement points according to the above equation. As shown, each of the six sensors 330–335, which preferably take the form of conducting plates, functions to measure an electric potential in the form of a respective voltage $V_1$–$V_6$ at its geometric center. More specifically, sensors 330–335 are linked and maintained at fixed relative positions through respective support arms or rods 340–345 to a main body or housing 350 through insulators, such as that indicated at 352 for support arm 340. In accordance with this form of the invention, housing 350 is formed from attaching three individual sensor modules 355–357, with sensors 330 and 331 being carried by module 355; sensors 332 and 333 being carried by module 356; and sensors 334 and 335 being carried by module 357. Support arms 340 and 341 are preferably coaxially aligned along a first axis, while support arms 342 and 343 extend coaxially along a second axis and support arms 344 and 345 extend coaxially along a third axis. As shown, the second axis associated with support arms 342 and 343 is arranged substantially perpendicular to the first and third axes.

Housing 350 also includes first and second end caps, one of which is indicated at 370. Within housing 350 is the electronics (not shown) associated with sensor system 300. Also projecting from each module 355–357 are respective electrical connectors, such as those indicated at 380–382 for module 355. Electrical connectors 380–382 are provided to link each module 355–357 of housing 350 to electrical components employed in reading and evaluating the signals received from sensor system 300. In addition, each module 355–357 includes an associated power switch, such as power switches 385 and 386 for modules 355 and 356 respectively. At this point, it should be understood that housing 350 could be integrally constructed, while employing only one set of electrical connectors 380–382 and one power switch 385, 386.

With this arrangement, electric fields are constructed in the following manner: $E_X=k_x(V_1-V_2+V_5-V_6)/2$, $E_Y=k_Y(V_3-V_4)$, $E_z=k_Z(V_1+V_2-V_5-V_6)/2$ in which the plate voltages $V_i$ and the constants $k_i$ are determined by calibration in a known electric field prior to actual use of sensor system 300. By virtue of the design of the capacitive-type, multi-component electric field sensor system 300 represented in FIG. 6, the three measured field components Ex, Ey and Ez intersect centrally in modules 355–357 of housing 350. However, it should be noted that the individual sensing arrays established by sensors 330–335 need not be arranged perpendicular with respect to each other, but rather only sufficient projection in orthogonal directions is needed to estimate the fields in those orthogonal directions.

As indicated above, electric field sensors 330–335 are spaced by arms 340–345 and insulators 352. In accordance with a preferred embodiment of the invention, each insulator 352 actually defines a magnetic field sensor, preferably an induction-type magnetic field sensor. Therefore, sensor system 300 preferably includes a corresponding number of magnetic field sensors 352 as electric field sensors 330–335. Positioning magnetic field sensors 352 in the manner set forth above enables magnetic field sensors 352 to perform a dual function of insulating the electric field sensors 330–335 and sensing various vector components of a given magnetic field. Although separate insulators and magnetic field sensors could be employed, this arrangement contributes to the compact nature of sensor system 300, while also minimizing costs. In any case, sensor system 300 can advantageously sense both electric and magnetic fields and, more specifically, vector components of each of electric and magnetic fields. Integrating the E and B sensor hardware obviously results in a smaller, lighter and less expensive system. These are significant benefits in their own right and make possible some applications, such as deployment of sensor system 300 on an aircraft.

At this point, it should be noted that support arms 340–345 could actually define the magnetic field sensors, while also spacing and insulating the various electric field (potential) sensors 330–335. In this case, the outer casing (not separately labeled) of each support arm 340–345 acts as the insulator. Instead, a separate insulator could be employed to carry a respective electric field sensor 330–335. In any case, the magnetic field sensors are shown as structural extensions between housing 350 and electric field sensors 330–335 which adds to the compact nature of the overall sensor system.

Figure 2:
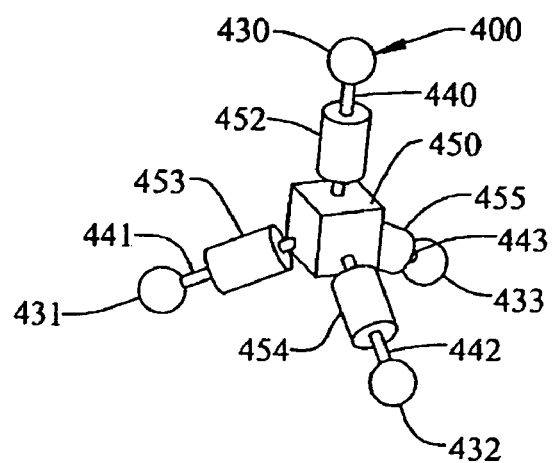
FIG. 2 is a perspective view of an integrated E and B sensor system constructed in accordance with another embodiment of the invention that measures non-orthogonal components of electric and magnetic fields.

FIG. 2 shows an integrated electric and magnetic field sensor system 400 constructed in accordance with another embodiment of the invention. Sensor system 400 is basically presented to illustrate that the field measurements need not be made along purely orthogonal axes. Instead, if desired, the field components in orthogonal directions can be calculated via simple geometry by methods well known in the art. To this end, note that sensor system 400 includes sensors 430–433, a housing 450, support arms 440–443 and magnetic sensors/insulators 452–455. With this arrangement, various components of both electric and magnetic fields can be sensed by sensors 430–432 and 452–455 respectively, with the signals therefrom being processed to establish orthogonal field measurements through simply knowing the geometrical relationship between the respective sensors 430–433, 452–455. Therefore, sensor system 400 can operate in a manner corresponding to sensor system 300, with fewer support arms and sensors, while requiring some mathematical manipulation of the signals to arrive at corresponding processed field data.

Figure 3:
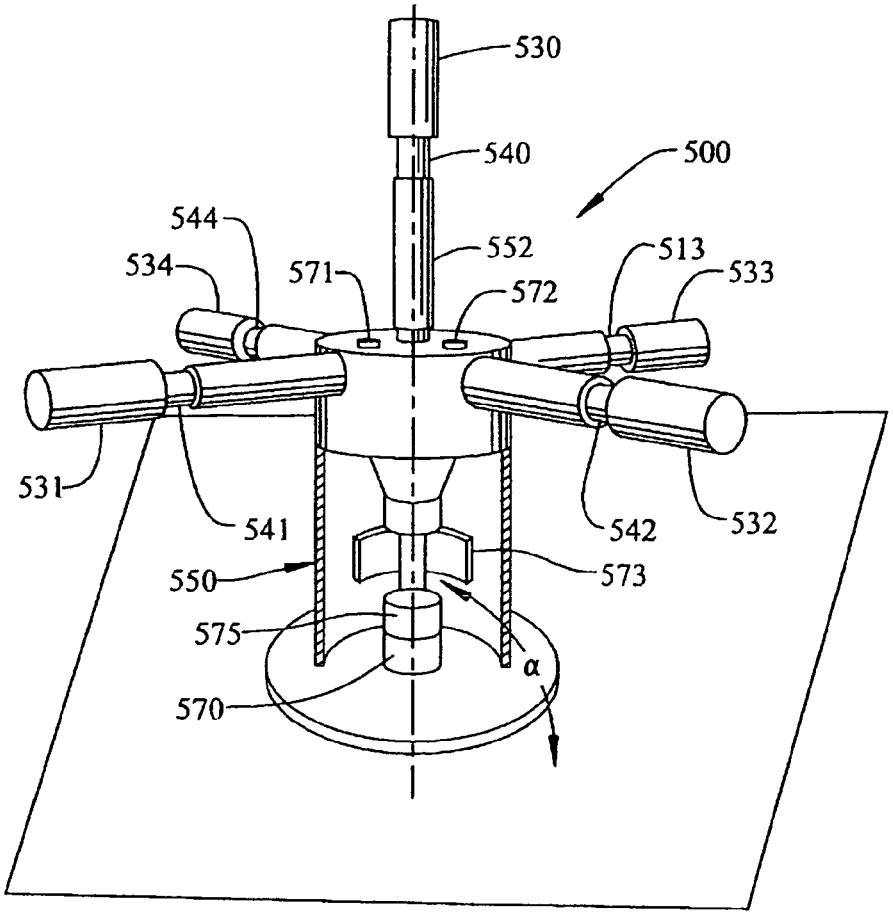
FIG. 3 is a perspective view of an integrated sensor constructed in accordance with a still further embodiment of the invention.

FIG. 3 presents the most preferred embodiment of the invention wherein a sensor system 500 includes a plurality of electric field sensors 530–534 which are supported from a generally puck-shaped housing 550 through respective support arms 540–544. Each support arm 540–544 also has associated therewith a respective magnetic sensor, one of which is indicated at 552 for support arm 540, that also functions as an insulator. The electric potential sensor is now self-contained in the sense that the first stage high input impedance electronics that was formerly located in housing 350 is now located with housing 530. The difference in the outputs of these sensors can be combined as in Equation 1 set forth above, to produce the value of the E-field between them.

Sensor system 500 shows a total of five electric potential sensors 530–534. In this embodiment, the field along the vertical axis of the sensor is calculated by subtracting the output of sensor 530 from the average of the outputs of sensors 531–534. If desired, a sixth sensor (not shown) can be positioned at the bottom end of the magnetic sensor 552 to provide a single measurement point for the second potential measurement along the vertical axis. The advantage of the five sensor embodiment 500 shown in FIG. 3 is that, by not having a sensor in the lower part of the system, a mounting means can be positioned there instead.

As with the other embodiments disclosed, sensor system 500 is preferably battery powered. The signals recorded by each sensor 530–534, 552 is made relative to the battery voltage that powers sensor system 500. When the common points of the batteries of any two sensors are connected together, the difference of the sensor outputs gives a reading directly proportional to the particular field. In a preferred version of the multi-axis, multi-field system, a DC battery unit 570 is used for sensors 530–534 and 552, thereby ensuring that all measurements are relative to a common reference. In any case, using the approach of FIG. 3 advantageously enables electric field sensors 530–534 and magnetic sensors 552 to be situated at any desired position.

The most preferred magnetic field sensor to use in the invention is a magnetic induction sensor that incorporates a high permeability material (the core) in order to concentrate magnetic flux. When suitably designed, such a sensor has the highest sensitivity of all types of room temperature magnetic field sensors. For example, a sensitivity of 0.2 pT/Hz$^{1/2}$ at 10 Hz and 0.03 pT/Hz$^{1/2}$ at 100 Hz can be achieved using a device less than 50 cm in length and 2 cm in diameter. To integrate two more such sensors together so that they intersect at their midpoints with minimal lateral offset (less than 1 cm), it is important to design the sensor with the minimum outer diameter and also to split the sensor winding so that the sensor midpoint has a cross-section only a little larger than the high permeability core material. By minimizing the lateral offset, the orthogonality between sensor outputs is maximized. A compact integrated magnetic induction sensor system so designed is an ideal sensor unit for use with electric field sensors in the manner shown in FIG. 3 and, in addition, can be used as a multi-axis highly sensitive magnetic field sensor in its own right.

FIG. 3 also illustrates other potential features of the sensor system of the present invention. More specifically, the sensor system 300, 400, 500 of the invention could also incorporate a global positioning system (GPS) 571 including a receiver and/or transmitter (not separately labeled) for use in connection with timing and position information. In addition, a sensing unit 572 can be provided to determine the actual orientation and tilt of sensor system 300, 400, 500. Such a sensing unit 572 is known in other arts so will not be described further here. By way of example, sensing unit 572 is employed in determining the tilt angle α of a predetermined axis of sensor system 300, 400, 500 relative to a plane substantially parallel to the earth's surface when the invention is utilized in a geophysical environment. Sensor system 300, 400, 500 also preferably includes a data storage pack 573 for storing electric and magnetic field data which can be transmitted through either wired or wireless connections.

As the particular circuitry employed in connection with the sensor system is not part of the present invention, it will not be described in detail here. However, FIG. 4 generally illustrates basic aspects of the present invention wherein both electric and magnetic field data is sent to a controller 575 in order that the signals can be processed to determine one or more vector components of the electric and/or magnetic field as represented by magnitude data 580 and direction data 585. On a general note, a high-impedance amplifier is preferably connected to each sensor. The amplifier is configured to buffer the output of the sensor and send a representative signal to a subsequent low-impedance circuit. In any case, each sensor is preferably modulated in time in order to increase its sensitivity.

In many cases, a considerable benefit of using both E and B sensors is not just to collect their individual outputs separately, but rather to combine their outputs to provide an integrated, processed electromagnetic system output. The capability to provide an integrated multi-axis electric field measurement is itself advantageous, and the further integration of electric field measurement with one or more axes of magnetic field measurement as set forth in accordance with the present invention provides additional measurement schemes which result in specific electromagnetic sensing opportunities. As will be detailed more fully below, the electric and magnetic field data can be synthesized to reduce the amount of output by combining channel data, while yielding improved fidelity by exploiting specific physical relationships between E and B data for specific targets and environmental conditions.

It is generally desired to combine the particular components of the E and B fields measured relative to the terrestrial frame of reference. Specifically, it is important to determine the vertical component ($E_z$, $B_z$) and/or the horizontal components, ($E_h$, $B_h$) of each field. Such a measurement can be arranged by aligning the sensor system along the axis of maximum gravitational field such that the desired sensor axis is situated in a desired orientation, or by mathematically rotating the output of multiple sensor channels to synthesize a desired measurement, using information from either a separate sensor or an internal calibration arrangement to determine the orientation of the sensor system. A general case is to compute the correlation between different pairs of E and B sensor data. This approach relies upon the fact that the predominant cause of E-field noise is the motion of airborne charged dust and particulates, while the predominant cause of B-field noise is the motion of the sensor itself due to seismic induced vibration or wind buffeting. These noise sources are not generally correlated in a time domain, and so they will not appear in a correlated output. This method is particularly effective when looking at electromagnetic transients (pulses in E and B) that are produced by some sources. The general expression for the correlation of two continuous time domain signals g and h is given by:

$$Corr(g, h) \equiv \int_{-\infty}^{\infty} g(\tau + t) h(\tau) d\tau$$

The parameter t is a lag applied to one of the signals, generally used as a method to determine at what offset the two signals are most common (i.e. have the highest correlation). For the application of noise rejection in two simultaneous signals the value of t will be 0 so the equation simply becomes $$Corr(g, h) \equiv \int_{-\infty}^{\infty} g(\tau) h(\tau) d\tau$$

The discrete form of the equation is then given by $$Corr(g, h) \equiv \sum_{k=0}^{N} g_k h_k$$

where N is the interval over which the correlation is considered. To account for varying values of N and differences in signal amplitudes, the correlation is often normalized as such:

$$Corr(g, h) \equiv \frac{\sum_{k=0}^{N} g_k h_k}{\frac{1}{N+1} \sqrt{\sum_{k=0}^{N} g_k^2 \sum_{k=0}^{N} h_k^2}}$$

[1] E. C. Ifeachor, B. W. Jervis, Digital Signal Processing: a practical approach, 1993, p. 189

Another integrated electric and magnetic measurement according to the invention is to compute the coherence between the horizontal components of E ($E_x$, $E_y$) and B ($B_x$, $B_y$). The advantage of this method is that it is generally easier to position sensors in the horizontal plane by taking advantage of the ground surface or by the aspect ratio of a wing structure for an airborne platform. A vertical sensor is susceptible to increased wind induced noise in dependence upon the extent the sensor projects above the ground and, at least in many cases, burying the sensor is not practical. The benefit of taking the coherence between horizontal channels is that, at the high sensitivity provided by the invention, horizontal B-field sensors are limited at low frequency by geoatmospheric (GA) noise. However, there is no GA noise in horizontal E-field sensors and so the noise is not coherent. This method provides an increased signal to noise ratio (SNR) in cases when the signal of interest is present in both $E_h$ and $B_h$. Coherence is expressed as $$\gamma = \frac{|S_{XY}|}{\sqrt{S_{XX} S_{YY}}}$$

Where $S_{XY}$ is the cross spectral density between the two signals x[t] and y[t] and $S_{XX}$ and $S_{YY}$ are the autospectra, while X(f) and Y(f) are the Fourier transforms of the two measured variable x[t], y[t], and Y'(f) is the complex conjugate of Y(f).:

$$\gamma = \frac{|X(f) Y'(f)|}{\sqrt{|X(f)|^2 |Y(f)|^2}}$$

A further integrated electric and magnetic measurement according to the invention is to input the data from both components of horizontal B ($B_x$, $B_y$) and vertical E ($E_z$) in a coherent canceling algorithm. The method relies on the fact that $B_h$ and $E_z$ both contain coherent GA noise, which is then cancelled. The method is suitable for sources that, due to their configuration, produce horizontal B but minimal $E_z$, or vice versa. A suitable such cancelling algorithm is a Wiener filter which provides the set of optimum coefficients to subtract an estimation of the noise alone, $x_k$, from a noise-contaminated signal $y_k$:

$$W_{OPT} = \frac{E[y_k X_k]}{E[X_k X_k^T]}^2$$

[2] E. C. Ifeachor, B. W. Jervis,

Digital Signal Processing: a practical approach, 1993, p. 548

Where E[ ] symbolizes the expected value. $E[y_k X_k]$ is the N length cross-correlation vector and $E[X_k X_k^T]$ is the N×N autocorrelation matrix (N being the number of filter coefficients). The output signal of the filter is then:

$$e_k = y_k - \sum_{i=0}^{N-1} w(i) x_{k-i}$$

This is the optimal filter and can be made adaptive by continuously updating the correlation vectors. Various types of Least Mean Square algorithms can be used to modify the set of filter coefficients on a sample-by-sample basis to achieve an estimation of the optimum set that adapts to changing noise characteristics.

A still further electric and magnetic integrated measurement algorithm is, in a sense, the inverse of the just prior method and applies to situations in which a vertical sensor direction is made easy by an implanted stake or preexisting vertical structure. The core idea is to calculate the coherence between vertical B and horizontal E. Vertical B is generally limited by vibration-induced noise owing to the way and upright sensors couple to seismic ground motion, as well as the increased wind force in the event that the sensor protrudes above the ground. $E_h$ has negligible vibration induced noise and so an algorithm that produces the coherence between $B_z$ and $E_h$ will have negligible vibration signals and so reduced noise.

The above-described control arrangements are particularly suited to primarily magnetic sources because such sources also generate horizontal and vertical electric fields via the electric currents they induce in the ground. Such sources can be either above ground or below ground. In some cases it is important to distinguish between a signal produced in the ground and a man-made signal produced remotely and traveling through the air. An example of this is to remove interference from above ground power lines from a measurement to locate a buried power cable.

A still further control arrangement according to the invention is to input a measurement of $E_z$ into a coherent canceling algorithm to remove above ground power line interference from horizontal E-field and/or B-field data. This method relies on the fact that the electric field produced by an above ground source is predominantly only in the vertical direction due to the conductivity of the earth. Based on the above description, it should be appreciated that, in a multi-axis integrated electric and magnetic sensor system as described by the invention, one or more of the measurement arrangements described above can be employed simultaneously in parallel. In addition, the noise reduced data produced by one arrangement can be used as inputs to other control functions to provide further improvements.

Figure 4:
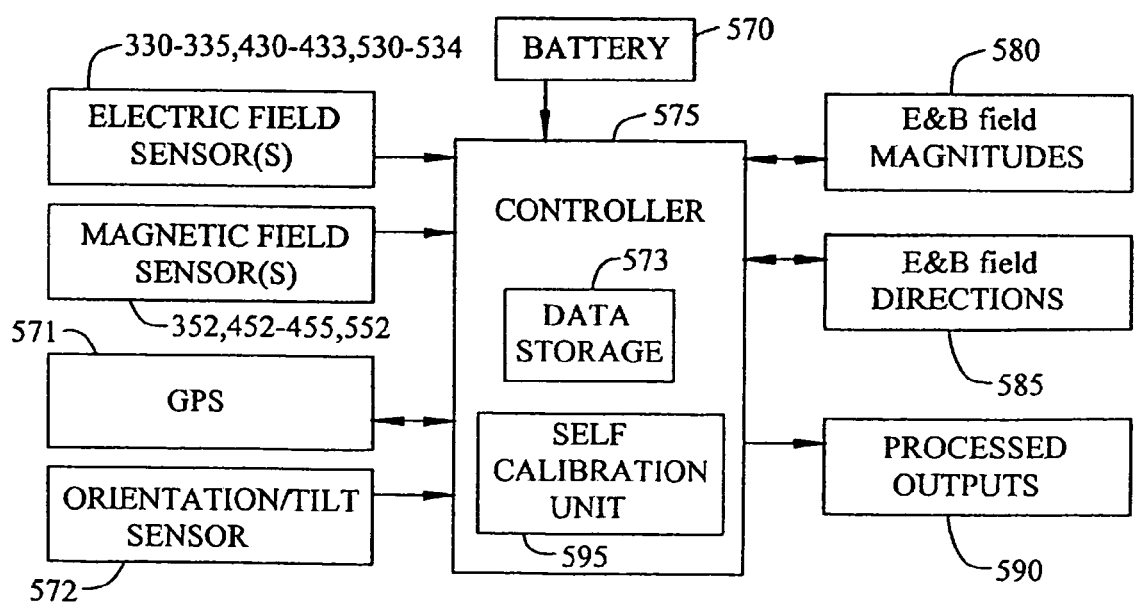
FIG. 4 is a block diagram illustrating control aspects of the invention.

As indicated above, the detected electric and magnetic field data can be separately stored and/or outputted, or further processed by controller 575, such as combining the various data in the ways discussed above, in order to establish processed data outputs as represented in FIG. 4 at 590. In many practical situations, it is very desirable to be able to confirm that a sensor is operating at its intended performance level and has not been damaged or otherwise become compromised. Furthermore both electric and magnetic field sensors can be strongly affected by being placed in close proximity to natural objects. For example, if an E-field sensor is close to a large conducting object, the field in its local vicinity will be distorted. Another scenario is a change in the coupling efficiency at the sensor input. If the sensor is placed on uneven ground so that one E-field detection surface is much closer to the ground than the others, the effective capacitance of this sensor will be altered and the fraction of the free space field coupled into the sensor changed. Another such scenario concerns the presence of a film of water on the sensor might act to provide an impedance to ground at its input or a shorting impedance between two sensors. In the case of a B-field sensor such effects could occur if the sensor is located in close proximity to a highly permeable object, such as an iron plate in the ground, or very high permeability soil.

A preferred method to monitor these effects is to provide a means on the sensor to create local electric and/or magnetic fields (represented by self-calibrating unit 595 in FIG. 4). An electric field can be produced by a small conducting surface driven at a desired potential, and a magnetic field produced by a small coil wrapped about the body of the sensor and carrying a desired current. These surfaces and coils are made small enough so as to be integrated into the body of the sensor, and not be externally visible. In both cases, the frequency of the potential or current can be swept over a desired range to provide a measure of the frequency response of the sensor of interest. The conducting surfaces and coils are connected rigidly to the sensor so that their positions and couplings will not change under normal operating conditions.

The system calibration is established before use under controlled conditions. Once the sensor is placed in a desired position, the calibration routine can be run as desired to confirm that the sensor is still operational in that it measures the known generated fields. If an improper or no response is detected, it is immediately obvious. Moreover if a small frequency dependent deviation is observed from the expected response, then this deviation can be use to provide diagnostic information as to the source of the problem. In some case the measured data can be corrected by the modified response function to give a more accurate record of the field measured by the sensor.

Although described with reference to preferred embodiments of the invention, it should be readily understood that various changes and/or modifications can be made to the invention without departing from the spirit thereof. For instance, although the embodiments described above are directed to combination electric and magnetic field sensor systems, some benefits can be realized in connection with integrating a plurality of magnetic field sensors which can determine a vector field component of a magnetic field. In any case, the sensor system is compact in nature and highly sensitive, with the sensor system having a maximum dimension of less than 100 cm, the E-field sensors having sensitivities relative to their input in the range of about 1 mV/Hz$^{1/2}$ at 1 Hz and the B-field sensors having sensitivities of at least 5 pT/Hz$^{1/2}$ at 10 Hz and 0.4 pT/Hz$^{1/2}$ at 100 Hz. In another preferred embodiment, a higher B-field sensor sensitivity of 3 pT/Hz$^{1/2}$ at 10 Hz and 0.3 pT/Hz$^{1/2}$ at 100 Hz with a maximum dimension of less than 20 cm is achieved. In a still further embodiment, a very high B-field sensor sensitivity of 0.2 pT/Hz$^{1/2}$ at 10 Hz and 0.03 pT/Hz$^{1/2}$ at 100 Hz with a maximum lateral dimension of less than 50 cm is established. Each magnetic field sensor preferably also includes two or more magnetic induction sensors that contain high permeability cores, wherein the plurality of magnetic sensors are arranged to intersect at a lateral offset of less than 1 cm. In any case, the invention is only intended to be limited by the scope of the following claims.

We claim:

1. An integrated sensor system for measuring electric and magnetic fields comprising:
   a plurality of electric field sensors;
   a plurality of magnetic field sensors;
   a housing supporting the plurality of electric and magnetic field sensors;
   a controller for determining at least one vector field component based on signals received from both the plurality of electric and magnetic field sensors; and
   means for combining field data by utilizing at least one of electric field data to modify magnetic field data and magnetic field data to modify electric field data.

2. The sensor system according to claim 1, wherein the plurality of magnetic field sensors function as at least one of structural and insulating elements for the plurality of electric field sensors.

3. The sensor system according to claim 1, wherein the sensor system is compact in nature and highly sensitive.

4. The sensor system according to claim 1, further comprising: a DC power source provided in housing, wherein the sensor system is self-contained and portable.

5. The sensor system according to claim 1, further comprising: a global positioning system for providing timing and positioning information.

6. The sensor system according to claim 1, further comprising: means, incorporated into the sensor system, for determining orientation and tilt information on the sensor system.

7. The sensor system according to claim 1, wherein the plurality of magnetic field sensors extend along three orthogonally arranged axis.

8. The sensor system according to claim 1, wherein said combining means utilizes electric field data from at least one of the plurality of electric field sensors to modify electric field data from at least another one of the plurality of electric field sensors.

9. The sensor system according to claim 1, wherein the plurality of magnetic field sensors have associated axes, with the axes intersecting at a center.

10. The sensor system according to claim 1, wherein at least two of the plurality of magnetic field sensors are arranged along an axis in common with at least one of the plurality of electric field sensors.

11. The sensor system according to claim 10, further comprising:
a plurality of arms projecting from the housing, each of the plurality of arms supporting a respective one of the plurality of electric field sensors, as well as a respective one of the plurality of magnetic field sensors.

12. The sensor system according to claim 11, wherein the plurality of arms includes first and second sets of arms, with the first and second sets of arms extending in distinct orthogonal directions.

13. The sensor system according to claim 11, wherein the plurality of arms includes first and second sets of arms, with the first and second sets of arms intersecting at angles of less than ninety degrees.

14. An integrated sensor system for measuring electric and magnetic fields comprising:
a plurality of electric field sensors;
a plurality of magnetic field sensors;
a housing supporting the plurality of electric and magnetic field sensors;
a controller for determining a vector field component based on signals received from both the plurality of electric and magnetic field sensors; and
means for self-calibrating the sensor system, said self-calibrating means producing local electric and magnetic fields.

15. A method for measuring electric and magnetic fields through an integrated sensor system comprising:
measuring electric field information along a plurality of distinct axes;
measuring magnetic field information along at least some of the plurality of distinct axes; and
combining the electric and magnetic field information to establish a processed output, with the processed output including at least one of magnetic and electric field data which has been modified based on at least one of the electric and magnetic field information.

16. The method of claim 15, further comprising: determining positioning information for the sensor system through a global positioning system.

17. The method of claim 15, further comprising: determining orientation and tilt of the sensor system.

18. The method of claim 15, further comprising: self-calibrating the sensor system.

* * * * *